United States Patent [19]

Rinner

[11] Patent Number: 5,683,394
[45] Date of Patent: Nov. 4, 1997

[54] FUSION MASS CONSTRAINER

[75] Inventor: James A. Rinner, Fountain Valley, Calif.

[73] Assignee: Advanced Spine Fixation Systems, Inc., Irvine, Calif.

[21] Appl. No.: 537,077

[22] Filed: Sep. 29, 1995

[51] Int. Cl.$^6$ .................................................. A61B 17/58
[52] U.S. Cl. ............................................ 606/86; 606/61
[58] Field of Search ................................ 606/86, 60, 61; 623/17, 16

[56] References Cited

U.S. PATENT DOCUMENTS

| | | | |
|---|---|---|---|
| 4,691,740 | 9/1987 | Ray et al. | 606/61 |
| 4,834,757 | 5/1989 | Brantigan | 623/17 |
| 4,878,915 | 11/1989 | Brantigan | 623/17 |
| 5,015,247 | 5/1991 | Michelson | 606/61 |
| 5,026,373 | 6/1991 | Ray et al. | 606/61 |
| 5,055,104 | 10/1991 | Ray | 606/61 |
| 5,263,953 | 11/1993 | Bagby | 606/61 |
| 5,458,638 | 10/1995 | Kuslich et al. | 623/17 |

*Primary Examiner*—Michael Buiz
*Assistant Examiner*—Daphna Shai
*Attorney, Agent, or Firm*—Christie, Parker & Hale, LLP

[57] ABSTRACT

A bone fusion mass constrainer is useful for promoting fusion between a pair of adjacent vertebrae. The bone fusion mass constrainer includes a generally cylindrical cage assembly having an internal cavity with open top and bottom surfaces. The cage portion is intended to be positioned in contact with the cancellous bone of the adjacent vertebrae. A pair of horizontal platforms extend out from the cage assembly and provide support for the vertebrae by contacting the harder cortical bone of the endplates of the vertebrae. Bone graft is inserted into the cavity where it contacts the cancellous bone of the adjacent vertebrae and promotes fusion between the two vertebrae. An end cap is provided over the proximal opening of the cage assembly to prevent migration of bone graft out from the cage. The bone fusion mass constrainer also includes a pair of blades which can be extended outwardly from the cage assembly and into the cancellous bone of the adjacent vertebrae in order to prevent migration of the device from between the vertebrae.

12 Claims, 6 Drawing Sheets

FUSION MASS CONSTRAINER

FIELD OF THE INVENTION

This invention is directed to a device for treatment of spinal column disorders such as ruptured or degenerated discs. More specifically it relates to a bone fusion mass constrainer sometimes referred to as a "bone cage" that can be inserted between the two vertebrae immediately adjacent the injured disc. The fusion mass constrainer is designed to hold bone graft in place to promote arthrodesis or fusion of the adjacent vertebrae.

BACKGROUND OF THE INVENTION

Various techniques have been used to treat spinal disorders such as ruptured or degenerated discs in order to prevent the adjacent vertebrae from pressing together and pinching the spinal nerve roots that extend from the spinal column between the vertebrae. Generally, the injured disc must be surgically excised. In order to prevent nerve root compression or impingement, various methods have been developed to maintain proper vertebral spacing while at the same time promoting fusion of the adjacent vertebrae.

One method employs one or more bone cages to maintain vertebral spacing during bone fusion. Bone cages are often hollow cylindrical devices such as spirally wound springs that are threaded into a hole bored between the springs that are threaded into a hole bored between the adjacent vertebrae at the injured disc. By boring such a hole, the inner cancellous bone of the vertebrae is exposed. Bone graft is placed into the hollow portion of the bone cage. The openings in the walls of the bone cage permit the bone graft to fuse to the cancellous bone of the adjacent vertebrae.

One problem with the installation of such a bone cage is that the majority of the forces transmitted between the bone cage and the vertebrae are borne by the spongy cancellous bone which does not always provide sufficient support during fusion. Fusion can often take several months. Consequently, bone cages may tend to migrate from their proper position. For example, bone cages can bury themselves into the cancellous bone, which can cause a loss of spine height and can lead to nerve root impingement.

Some bone cages can also migrate in a horizontal plane. Depending on the forces pressing on the bone cage and the location at which the bone cage is provided along the spine, the cages can be pushed out either anteriorly, posteriorly or to either side. Such migration can cause a number of complications including nerve damage.

The problem with migration can sometimes be avoided by using additional instrumentation such as spine rods and pedicle screws that can be fastened to the adjacent vertebrae. However, such procedures significantly complicate the requisite surgical procedure and can lead to additional complications inherent to the use of such devices.

An improved bone fusion mass constrainer is desired for use in fusing a pair of adjacent vertebrae. It is imperative that such a device stay in place without migrating during the period of time required for proper bone fusion.

SUMMARY OF THE INVENTION

The bone fusion mass constrainer of the present invention includes a generally cylindrical cage assembly that is intended to be oriented with its axis generally perpendicular to a patient's spinal column. The cage assembly has an internal cavity with open top and bottom sections. Extending from the sides of the cage assembly are a pair of opposed platforms for providing additional support to the adjacent vertebrae at the bony cortical portions of their endplates.

In installing the device, a hole is bored into the space between the vertebrae to remove a portion of the hard cortical bone at the endplates of the adjacent vertebrae and expose the softer cancellous bone of the vertebrae. The cage assembly is then inserted between the adjacent vertebra. While the cage assembly extends into the cancellous portion of the vertebrae above and below the injured disc, the horizontal platforms extend laterally to support the outer section of cortical bone on the endplates of the vertebra and prevent migration of the cage assembly into the cancellous bone. Bone graft material is then inserted through an opening in a proximal end of the cage assembly and into the inner cavity. There, the graft material contacts the cancellous bone of the vertebrae above and below the cage assembly through the openings in the cage assembly. By exposing the bone graft to the cancellous portion of the vertebrae, fusion is encouraged.

The distal end of the cage assembly is closed to prevent the bone graft from migrating distally out from between the vertebra. Once the cavity has been packed with a sufficient quantity of bone graft, a cap is placed over the proximal opening of the bone cage assembly in order to prevent migration of the bone graft through the proximal opening. The end cap includes a pair of projecting blades, which extend into the cancellous bone of the adjacent vertebrae to anchor the assembled bone fusion mass constrainer and prevent its migration.

BRIEF DESCRIPTION OF THE DRAWINGS

Features, aspects and advantages of the invention will be more fully understood when considered with respect to the following detailed description, appended claims and accompanying drawings where:

DETAILED DESCRIPTION OF THE INVENTION

Figure 1:
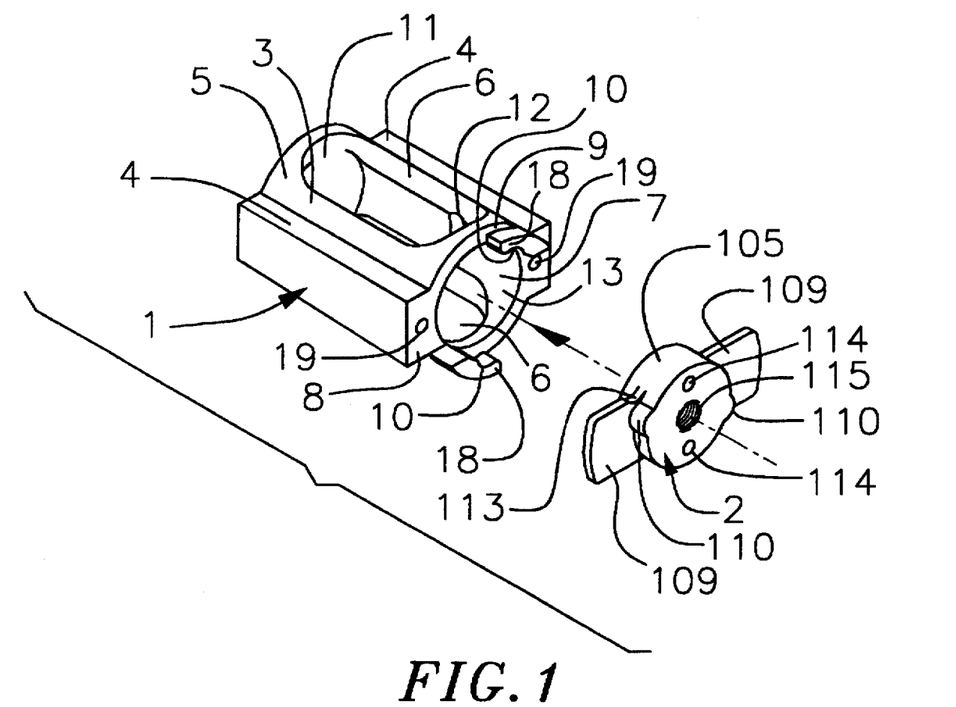
FIG. 1 is an exploded isometric view of a device of the present invention.
Figure 2:
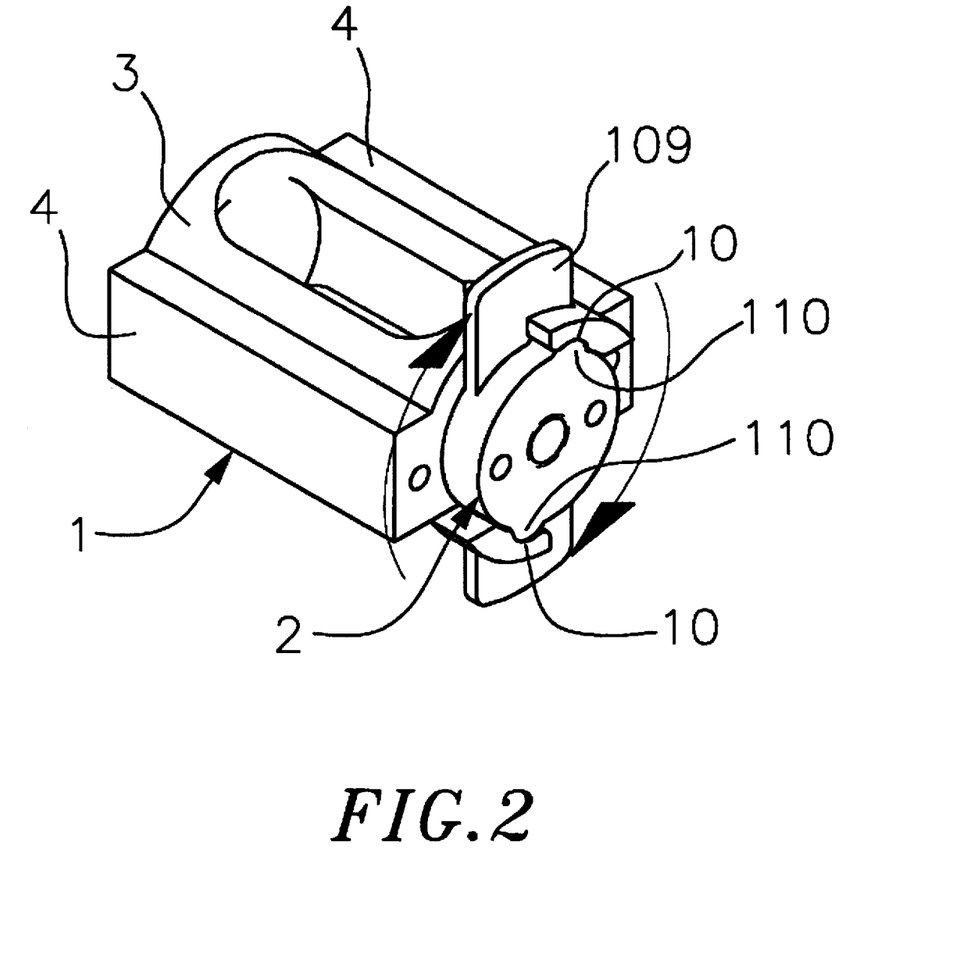
FIG. 2 is an isometric view of the device of FIG. 1 as assembled.
Figure 3:
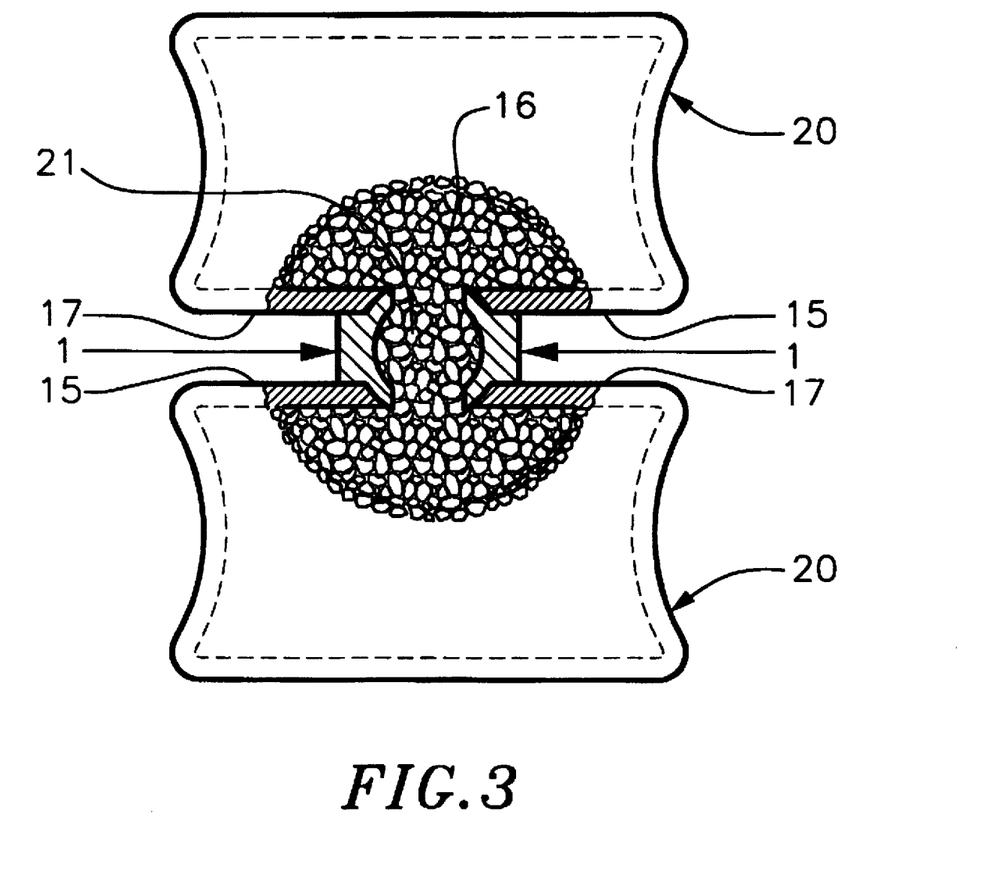
FIG. 3 is an elevation view partly in section of a device as implanted.

Referring to FIGS. 1-3, a fusion mass constrainer of the present invention is illustrated. The fusion mass constrainer includes a main body portion 1 that includes a hollow cage assembly 3 having an inner cavity 7. The cage assembly includes a generally cylindrical outer surface 5 that is meant to be arranged with its axis in a generally horizontal plane. The cage assembly has a pair of opposing horizontal platforms 4 of generally rectangular cross section which extend from the cage assembly along its length. The outer surface also includes a pair of openings 6, one above and one below the planes formed by the upper and lower surfaces of the platforms.

As shown in FIG. 3, the fusion mass constrainer of the present invention is to be installed between a pair of adjacent vertebrae 20 of a patient to encourage fusion between the vertebrae. First, a hole of about the same diameter as the diameter of the cage assembly of the fusion mass constrainer is bored into the space between the vertebrae. This removes a portion of the hard cortical bone 15 of the endplates 17 of the vertebrae both to allow the insertion of the fusion mass constrainer and to expose the cancellous bone 16 in the center of the vertebrae in order to encourage fusion.

The fusion mass constrainer is then inserted into this bore hole such that the cage assembly extends into the cancellous bone of the lower end plate of the vertebra above the injured disc, and into the cancellous bone of the upper face of the vertebra below the injured disc. The two horizontal platforms extend laterally and provide support for the vertebrae at the sturdy cortical portion of the endplates of the adjacent vertebrae.

Once inserted, the cavity of the cage portion is filled with bone graft 21. Autograft bone, allograft bone, synthetic or a matrix of materials can be used. The bone graft is inserted through a proximal opening 13 in the proximal face 8 of the main body portion (see FIG. 1). The top and bottom openings of the cage assembly are in open communication with the cavity to permit the cancellous bone to contact the adjacent vertebrae so as to allow absorption of the bone graft which will eventually lead to the fusion of the two adjacent vertebrae. The distal end 11 of the cage is closed to prevent migration of graft material out from the cage through that end.

Migration of bone graft from the proximal end of the cage is prevented by an end cap 2 which fits over and closes the proximal opening. The end cap includes a cylindrical portion 105 of approximately the same diameter as the cavity of the main body portion. A pair of blades 109 are provided integral to the end cap and extend out from opposite sides of the surface of the cylindrical portion.

The end cap is positioned by orienting the blades horizontally and inserting the cylindrical portion into the cavity of the main body portion. The end cap is then rotated in a clockwise direction approximately 90 degrees as best illustrated in FIG. 2. By rotating the blades in this fashion, the blades are forced into the cancellous bone of the vertebrae above and below the injured disc. Once rotated into place, the vertically oriented blades prevent migration of the fusion mass constrainer from its location between the vertebra.

The end cap is locked against outward motion by the blades interlocking with a pair of slots 9 on the main body portion (see FIG. 1). Clearance notches 113 on the blades allow the end cap to be rotated a full 90 degrees so that the blades are oriented in a vertical direction. A pair of fingers 18 extend from the main body portion to form the slots. The fingers include a pair of detent notches 10 on their inwardly facing surfaces which interlock with a pair of detent tabs 110 that extend out from opposite sides of the cylindrical surface of the end cap in front of the blades. The detent notches and detent tabs cooperate to prevent rotation of the end cap and lock it in position once the blades have been properly positioned.

In order to ease assembly of the end cap to the main body portion, the end cap includes a central threaded hole 115 for temporarily attaching an end cap tool (not shown) to hold the cap while it is placed over the main body portion. A pair of positioning holes 114 on the proximal face of the end cap receive a pair of pins extending from the end cap tool and permit rotation of the end cap into its final position as illustrated in FIG. 2.

In order to simplify insertion of the cage assembly between the vertebrae, the cage assembly includes a circumferential groove 12 inside the cavity as shown in FIG. 1. This groove receives an insertion tool (not shown) to simplify the insertion of the device. The tip of the insertion tool can be inserted into the cavity through the proximal opening and a plurality of ball bearings or pins can then be extended from the tip to hold the cage assembly at the groove. A pair of positioning holes 19 on the proximal face of the cage assembly cooperate with a pair of pins on the insertion tool to aid in locking the insertion tool to the cage assembly during insertion of the cage assembly.

The bone fusion mass constrainer of the present invention provides several advantages over other bone cages. One advantage is that the proximal opening to the inner cavity of the main body portion is of the same diameter as the inner cavity. This greatly simplifies the insertion of bone graft material by providing a clear path for its insertion. In order to promote good fusion, the cavity must be tightly packed with bone graft material.

Furthermore, the relatively large and unobstructed upper and lower openings of the cage assembly greatly encourage contact between the cancellous bone of the vertebrae to be fused and the bone graft material. This promotes absorption of the bone graft material. Unlike other bone cages with openings around their entire perimeter, by only including openings on the upper and lower surfaces of the bone fusion mass constrainer, migration of bone graft away from the cancellous bone of the vertebrae is prevented.

Another important benefit of the present invention is that the blades anchor the installed bone fusion mass constrainer between the vertebrae and prevent its migration. In many prior art bone cages, the forces acting on the patient's spine due to both the geometry of the spine and the weight carried by the spine could tend to push the bone cage out from between the vertebrae to be fused.

Another important advantage of the present invention is that the horizontal platforms provide an extremely stable construct. The platforms transfer the compressive forces between the spine and the bone fusion mass constrainer to the hard cortical bone of the vertebrae endplates rather than to the soft cancellous bone. This prevents vertical migration of the bone fusion mass constrainer into the cancellous bone. The stability provided by the device of the present invention encourages fusion by maintaining the vertebrae in a rigid, spaced position.

Figure 4:
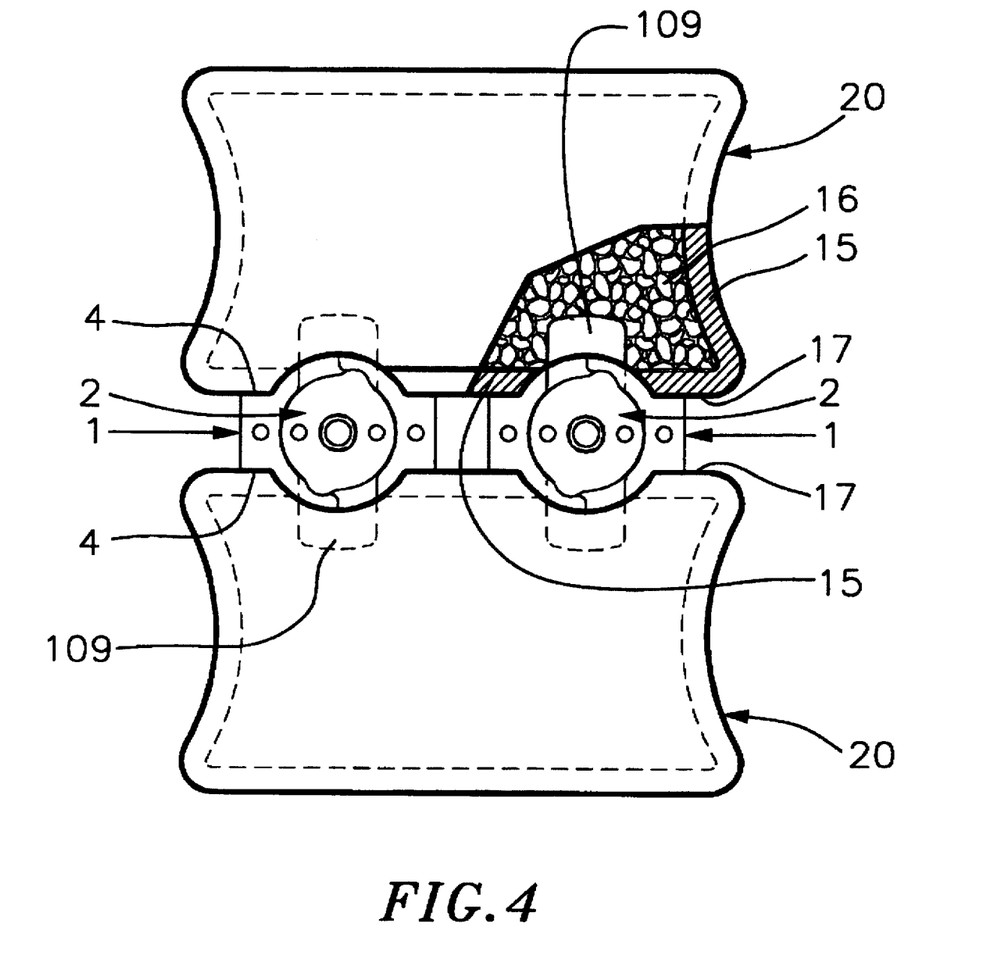
FIG. 4 is an elevation view partly in section showing a pair of devices as implanted.

While a single bone fusion mass constrainer is usually used, as illustrated in FIG. 3, a pair of bone fusion mass constrainers of the present invention can be used together side by side to bridge a pair of vertebrae during the fusion process as illustrated in FIG. 4.

Figure 5:
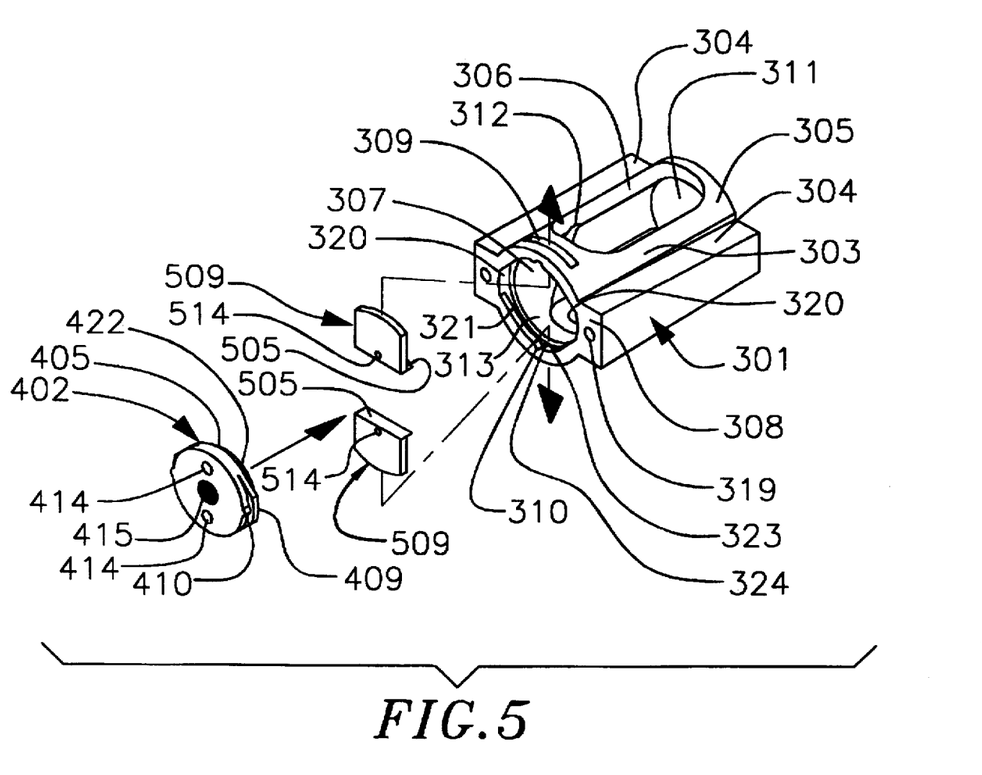
FIG. 5 is an exploded isometric view of a second embodiment of the device of the present invention.
Figure 6:
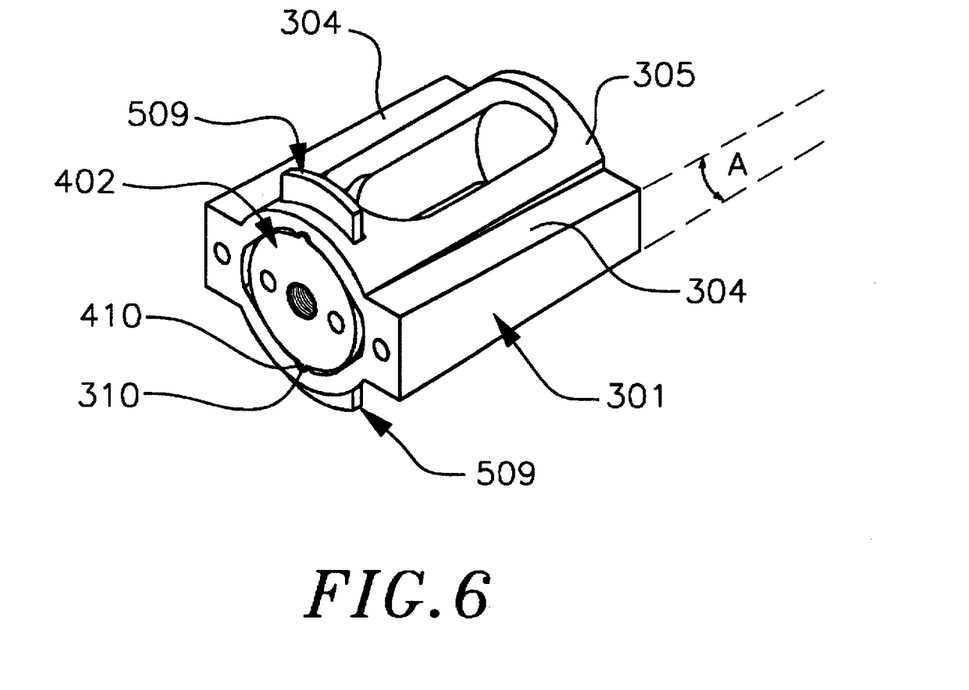
FIG. 6 is an isometric view of the device of FIG. 5 as assembled.
Figure 7:
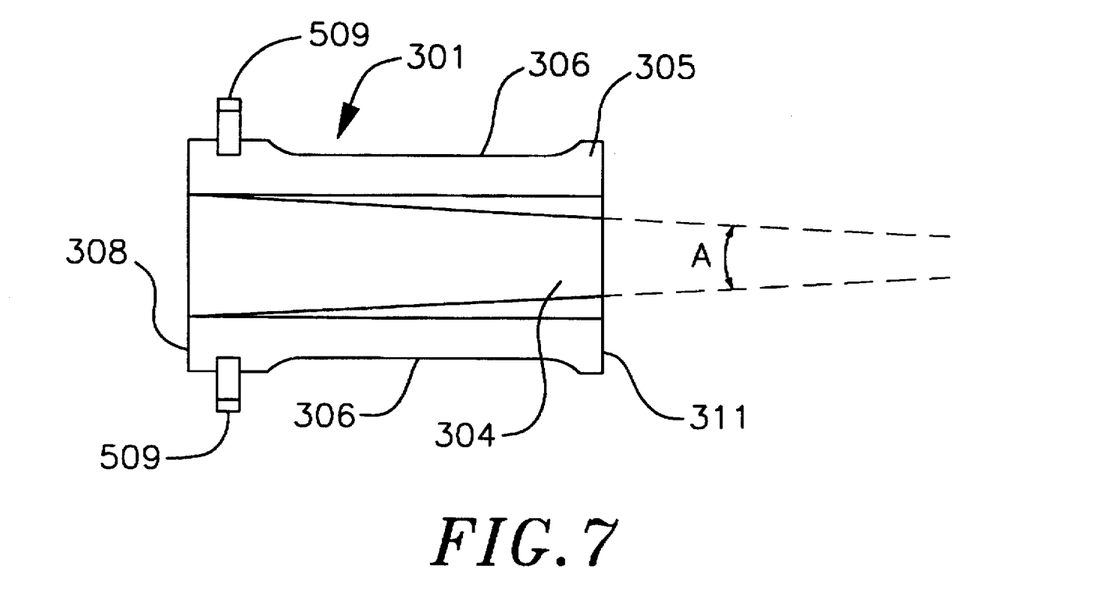
FIG. 7 is an elevation view of the device of FIG. 6.

A variation of the bone fusion mass constrainer of the present invention is illustrated in FIGS. 5–7. Similar to the first embodiment, its main body portion 301 includes a hollow cage assembly 303 having a generally cylindrical outer surface 305. A pair of openings 306 permit the bone graft which is inserted into an inner cavity 307 to contact the vertebrae to be fused. A proximal opening 313 on the proximal face 308 allows the insertion of the bone graft material while a closed distal end 311 prevents migration of the bone graft out from the inner cavity through the distal end.

Unlike the first embodiment, this bone fusion mass constrainer includes a pair of wedge shaped platforms 304 in which the upper and lower surfaces of each platform taper distally along the length of the platform. The angle formed between the upper and lower surfaces of the platforms can be selected so as to create or maintain a desired lordosis of the spine. In most instances, the angle "A" between the upper and lower surfaces is less than about 10 degrees (See FIGS. 6 and 7). The particular angle used will generally depend on the geometry of the spine for a particular patient.

The alternate embodiment of the bone fusion mass constrainer also includes a three-piece end cap and blade assembly rather than providing blades integral to the end cap. A pair of blades 509 are inserted into mating slots 309 formed in the main body portion of the bone fusion mass constrainer. The blades each include a stop 505 which prevents the blade from advancing all the way through the slot when inserted. An end cap 402 includes a generally cylindrical portion 405 which is approximately the same diameter as the cavity in the cage assembly. A pair of cams 409 extend outwardly from opposite sides of the cylindrical portion of the end cap.

As with the first embodiment, a hole is bored in the space between the vertebrae to be fused to expose the cancellous bone of the adjacent vertebrae. The main body portion of the bone fusion mass constrainer is then inserted into the bore hole and the inner cavity is packed with bone graft. A circumferential groove 312 within the inner cavity and a pair of positioning holes 319 permit the use of an insertion tool (not shown) to assist in inserting the main body portion.

The blades are then inserted into their respective slots and partially pressed into the cancellous bone. A positioning hole 514 on each blade simplifies the handling of the blades by allowing the use of a suitable tool. The end cap is oriented with the cams perpendicular to the blade orientation and is then pressed into place within the proximal opening. A circumferential groove 321 provided at the proximal opening includes a pair of opposed cutouts 320 for receiving the cams.

Once the end cap has been placed within the proximal opening, it is rotated about 90 degrees with the cams in the circumferential groove. The cams press against the stops of the blades to fully extend the blades into the cancellous bone of the adjacent vertebrae. A pair of detent tabs 410 extending out from opposite sides of the cylindrical surface of the end cap in front of the cams cooperate with a pair of detent notches 310 formed at opposite sides of the proximal opening in front of the circumferential groove to lock the end cap in place and maintain the blades in fully extended positions. The circumferential groove cooperates with the cams to prevent the end cap from being pushed outwardly. A central threaded hole 415 and a pair of positioning holes 414 allow the use of an end cap tool (not shown) to assist in handling the end cap and rotating it into position.

While this embodiment includes both wedge-shaped platforms and a three-piece end cap and blade assembly, it is clear that the specific features of the different embodiments can be effectively combined in many ways. For example, a cage assembly such as that disclosed in FIGS. 1-4 can be provided with wedge-shaped platforms for use with a one-piece end cap and blade design. Similarly, the embodiment with a three-piece end cap and blade assembly can be provided with platforms having parallel surfaces. Moreover, in either embodiment, wedge-shaped platforms can be provided in which the platforms taper in a proximal direction.

It is preferred that each of the parts that make up the bone fusion mass constrainer of this invention be machined from a solid piece of ASTM implantable material. Preferably, titanium or one of its alloys is used.

The present invention is not intended to be limited to the specific designs shown which are merely illustrative. Various and numerous other arrangements may be devised by one skilled in the art without departing from the spirit and scope of the invention. The scope of the invention is defined by the following claims.

What is claimed is:

1. A bone fusion mass constrainer for insertion between a pair of adjacent vertebrae to promote fusion between the vertebrae comprising:

a cage assembly defining an inner cavity for containing bone graft;

a pair of opposed platforms for providing support to the adjacent vertebrae;

a pair of blades extendable from the cage assembly for anchoring the cage assembly between the adjacent vertebrae; and an end cap for closing the inner cavity and including means for extending the blades from the cage assembly.

2. A bone fusion mass constrainer for insertion between a pair of adjacent vertebrae to promote fusion between the vertebrae comprising:

a cage assembly defining a longitudinal inner cavity with an open end and further defining a plurality of openings allowing communication between the inner cavity and the vertebrae to be fused;

a pair of opposed platforms extending from the cage assembly; and an end cap for closing the open end of the cage assembly, the end cap including a pair of blades for extending from the cage assembly into at least one of the vertebrae to be fused upon rotation of the end cap.

3. A bone fusion mass constrainer for insertion between a pair of adjacent vertebrae to promote fusion between the vertebrae comprising:

a generally cylindrical cage assembly, the cage assembly comprising:
  a longitudinal inner cavity;
  first and second ends, the first end being closed and the second end having a proximal opening in communication with the inner cavity; and
  a pair of surface openings through an outer surface of the cage assembly and into the inner cavity;

a pair of platforms extending longitudinally along the outer surface of the cage assembly and outwardly from the cage assembly;

an end cap for closing the proximal opening of the cage assembly; and a pair of blades integral to the end cap for extending outwardly from the cage assembly upon rotation of the end cap.

4. A method for promoting fusion between a pair of adjacent vertebrae comprising the steps of:

exposing a portion of the cancellous bone of each of the pair of vertebrae;

inserting a bone fusion mass constrainer between the vertebrae, the bone fusion mass constrainer having an inner cavity, and a pair of surface openings in communication with the inner cavity, the bone fusion mass constrainer placed such that the surface openings communicate with the cancellous bone of the pair of vertebrae;

inserting bone graft into the inner cavity; and extending a pair of blades from the bone fusion mass constrainer into the cancellous bone of the pair of vertebrae to anchor the bone fusion mass constrainer in place.

5. A bone fusion mass constrainer for insertion between a pair of adjacent vertebrae to promote fusion between the vertebrae comprising:

a cage assembly defining a longitudinal inner cavity with an open end and further defining a plurality of openings allowing communication between the inner cavity and the vertebrae to be fused;

a pair of opposed platforms extending from the cage assembly;

at least one blade extendable from the cage assembly into at least one of the vertebrae to be fused; and an end cap for closing the open end of the cage assembly and including means for extending the at least one blade from the cage.

6. The bone fusion mass constrainer of claim 5 wherein the means for extending the at least one blade comprises a cam.

7. The bone fusion mass constrainer of claim 5 wherein each of the pair of platforms defines a pair of parallel platform surfaces.

8. The bone fusion mass constrainer of claim 5 wherein each of the pair of platforms defines a first platform surface and a second platform surface, the first platform surfaces being at an angle of less than about 10 degrees from parallel to the second platform surfaces.

9. A bone fusion mass constrainer for insertion between a pair of adjacent vertebrae to promote fusion between the vertebrae comprising:

a generally cylindrical cage assembly, the cage assembly comprising:

a longitudinal inner cavity;

first and second ends, the first end being closed and the second end having a proximal opening in communication with the inner cavity;

a pair of surface openings through an outer surface of the cage assembly and into the inner cavity; and a pair of opposed slots;

a pair of platforms extending longitudinally along the outer surface of the cage assembly and outwardly from the cage assembly;

an end cap for closing the proximal opening of the cage assembly; and a pair of blades for extending outwardly from the slots of the cage assembly and into the vertebrae.

10. The bone fusion mass constrainer of claim 9 wherein the end cap includes a pair of cams for extending the pair of blades outwardly from the bone cage.

11. The bone fusion mass constrainer of claim 9 wherein each of the pair of platforms defines a first platform surface and a second platform surface, the first platform surfaces being at an angle of less than 10 degrees from parallel to the second platform surfaces.

12. The bone fusion mass constrainer of claim 9 wherein each of the pair of platforms defines a first platform surface and a second platform surface, the first platform surfaces being parallel to the second platform surfaces.

\* \* \* \* \*